United States Patent [19]

Alvila et al.

[11] Patent Number: 5,041,685
[45] Date of Patent: Aug. 20, 1991

[54] PROCEDURE FOR PRODUCING ALCOHOLS AND ALDEHYDES FROM ALKENES AND SYNTHESIS GASES

[75] Inventors: Leila Alvila, Joensuu; Outi Krause, Espoo; Tapani Pakkanen; Tapani Venäläinen, both of Joensuu, all of Finland

[73] Assignee: Neste Oy, Finland

[21] Appl. No.: 424,289

[22] PCT Filed: Mar. 22, 1989

[86] PCT No.: PCT/FI89/00055

§ 371 Date: Oct. 25, 1989

§ 102(e) Date: Oct. 25, 1989

[87] PCT Pub. No.: WO89/09201

PCT Pub. Date: Oct. 5, 1989

[30] Foreign Application Priority Data

Mar. 22, 1988 [FI] Finland .................................. 881361

[51] Int. Cl.$^5$ .............................................. C07C 45/50
[52] U.S. Cl. .................................... 568/455; 568/454; 568/882
[58] Field of Search ............... 568/451, 454, 455, 840, 568/882

[56] References Cited

U.S. PATENT DOCUMENTS

| | | | |
|---|---|---|---|
| 2,820,059 | 1/1958 | Hasek et al. | 568/455 |
| 3,231,621 | 1/1966 | Slaugh | 568/455 |
| 3,594,425 | 7/1971 | Brader, Jr. et al. | 260/604 |
| 4,127,506 | 11/1978 | Gray et al. | 568/455 |
| 4,238,358 | 12/1980 | Pesa et al. | 568/455 |
| 4,306,842 | 12/1981 | Pettit | 568/455 |
| 4,469,895 | 9/1984 | Knifton et al. | 568/454 |

FOREIGN PATENT DOCUMENTS

| | | | |
|---|---|---|---|
| 725670 | 1/1966 | Canada | 568/455 |
| 739007 | 7/1966 | Canada | 568/455 |
| 0163532 | 12/1985 | European Pat. Off. . | |
| 19428 | 9/1964 | Japan | 568/454 |
| 653 | 1/1966 | Japan | 568/455 |
| 992136 | 7/1961 | United Kingdom | 568/455 |

OTHER PUBLICATIONS

Journal of Molecular Catalysis, 29 (1985) pp. 77–98.

*Primary Examiner*—Werren B. Lone
*Attorney, Agent, or Firm*—Steinberg & Raskin

[57] ABSTRACT

The present invention concerns a procedure for preparing alcohols and aldehydes from alkenes and synthesis gas by a heterogeneous reaction in which the catalyst system is composed of $Ru_3(CO)_{12}$ and a heterocyclic base in suspension or absorbed in a fixed carrier.

5 Claims, No Drawings

PROCEDURE FOR PRODUCING ALCOHOLS AND ALDEHYDES FROM ALKENES AND SYNTHESIS GASES

BACKGROUND OF THE INVENTION

The present invention concerns a procedure for producing alcohols and aldehydes from alkenes and synthesis gases.

Oxygen containing compounds such as alcohols and aldehydes are generally produced by hydroformylation processes. The catalysts of industrial processes are typically homogeneous rhodium or cobalt carbonyls or phosphines. Heterogeneous catalysts can be produced by binding a metal compound on a fixed organic or inorganic carrier, whereby certain advantages are gained. The heterogeneous catalyst is easy and advantageous to separate from the products, which is specifically advantageous in using expensive rhodium catalysts. The heterogeneous catalyst is also thermally more stable than the homogeneous catalyst and causes less corrosion. In addition, the metal compound and the carrier may have useful combined effects. The processes of the homogeneous catalysts are however more specific and repeatable.

Metal cluster compounds are provided with advantageous characteristic features as precursors to catalysts because their specific structures as catalysts enable them to have better activities and particularly selectivities in comparison with simple metal complexes. The greatest difficulty is, however, the instability of metal cluster compounds. Advantages of heterogeneous cluster catalysts are lack of halides (a halide can be a catalytic toxic agent and cause aggregation and sintration), and provision of exact combination.

In the Finnish Patent No. 69620 is disclosed a catalyst for producing hydrogen gas from carbon monoxide and water (transfer reaction of aqueous gas). The catalyst is produced from the group VIII metal carbonyls and heterocyclic base. The metal carbonyl of the group is $Ru_3(CO)_{12}$, $FeRu_2(CO)_{12}$, $Fe_2Ru(CO)_{12}$, or their derivative $M_3(CO)_{12}\text{-}L_x$, in which M is Ru or Fe, x is 1 or 2, and L is a trialkyl or triaryl phosphine or phosphite. The heterocyclic base used is a 2,2'-bipyridine or 1,10 phenantroline.

SUMMARY OF THE INVENTION

As taught by the invention, the dissolvent containing the metal carbonyl compound and heterocyclic base was refluxed at 80° C., whereby an active complex was produced in the transfer reaction of the aqueous gas. The heterogeneous catalyst was produced directly on the surface of the carrier by heating at 100° C. protective gas or vacuum silicon gel in which cluster compound and base were impregnated. Thereby was produced a dark blue active catalyst. Advantages of the catalyst of the invention are outstanding activity and stability whereas a disadvantage sensitivity to air.

As taught by the invention, it has been found that from the above described metal cluster base system a new catalyst can be synthetized for producing alcohols or aldehydes from alkenes and synthesis gas by means of a hydroformylation reaction. Thus, the procedure of the invention for producing alcohols or aldehydes from alkenes and synthesis gas by means of hydroformylation reaction is characterized in that a gas mixture containing alkene, hydrogen and carbon monoxide is made to react at over 100° C. in the presence of the heterogenic catalyst system, comprising a solid catalyst compound produced from a cluster compound $Ru_3(CO)_{12}$ and from a heterogeneous base in a suspension, or bound on the surface of a solid carrier substance.

In the procedure of the invention is gained the surprising advantage that alcohols are produced in the hydroformylation at a high selectivity rate. In certain instances, from alkenes are produced almost exclusively alcohols. This is a very great improvement in comparison with conventional hydroformylation catalysts which merely yield either aldehydes or mixtures of aldehydes and alcohols, and thus require an extra processing phase for hydrating aldehydes into alcohols. In addition, with the procedure of the invention the desired direct-chain alcohol is obtained in a remarkably selective manner. The activity of the catalyst is also significant in hydroformylation of merely end-double-bound alkenes at 373° K.

In the catalyst system used in the procedure of the invention, the heterocyclic base can be selected from the group which contains, for instance 2,2' bipyridine, 2,3' bipyridine, 2,4' bipyridine: 6,2" terpyridine, and 1,10 phenanthroline, or compounds in which the aromatic ring system is composed of two or several nitrogen atoms. The best results are obtained when the base is a 2,2' bipyridine, whereby the conversion of alkenes into alcohols can be almost complete. Also other of these bases are useful, even though the conversion degree therein is lower. In that instance, the conversion degree may however be improved by returning part of the products back to the hydroformylation reaction.

The catalyst system used in the procedure of the invention can be prepared by mixing ruthenium carbonyl $Ru_3(CO)_{12}$ and a heterocyclic base, and heating the obtained complex system for obtaining an active catalyst. The heating temperature is not critical, and it may therefore vary between 50° to 200° C. An appropriate temperature has proven to be about 100° C. The heating needs to be performed either in a sheltering gas, for instance in nitrogen, or alternately, in vacuum, because the catalyst complex to be produced is sensitive to air.

In the procedure of the invention, the hydroformylation is performed in a heterogeneous phase, which means that the catalyst is not soluble in a solvent used possibly in the hydroformylation. An active catalyst complex may be applied in a heterogeneous hydroformulation reaction as such, whereby the hydroformylation is accomplished in suspension or performing the activation when the catalyst complex is absorbed in a carrier. For the carrier, it is advantageous to use inorganic silicon compounds, for instance silica gel or magnesium silicates, or other inert inorganic carriers, such as aluminium oxide. In the procedure of the invention, the heterogeneous hydroformylation can be accomplished either in liquid or gas phase. In the reaction can be used a solvent, for which the catalyst being used is non-soluble. For obtaining good results, the pressure and especially the temperature is required to be on a sufficiently high level. A recommendable pressure is at least 1 MPa, and the temperature is over 360° K. The hydroformulation temperature to be recommended is of the order 460° K.

The selectivity of formation of compounds containing oxygen, or alcohols and aldehydes, is high in the procedure of the invention, and no hydration of olefines takes place in the hydroformylation process. The nonreactive olefines can be easily separated from the products by distilling and circulating them back into the reactor. The reaction is extremely exothermal and therefore, it is advantageous to act on lower conversion levels.

The ruthenium concentration and $H_2$:CO ratio exerts an effect on the product distribution, that is, alcohols are most greatly produced when $H_2$:CO ratio is of the order 1:1.

The invention is described in the following more in detail with the aid of the embodiment examples.

EXAMPLE 1

A catalyst was prepared by mixing 3.0 g silicon dioxide (silika grades F-22), 0.096 g $Ru_3(CO)_{12}$, 0.073 g 2,2′ bipyridine, and 50 ml $CH_2Cl_2$. The solvent was evaporated, the catalyst was transferred into an airproof metal tube and rinsed with nitrogen. The catalyst was activated by heating the metal tube at 100° C., whereby in the carrier was produced a blue active compound.

EXAMPLE 2

A catalyst was prepared as in Example 1, with the exception that of the carrier was used 1.0 g and of $Ru_3(CO)_{12}$, 0.1 g.

EXAMPLES 3 AND 4

The catalysts were prepared as in Example 1, with the exception that in Example 3 the carrier was Davison silika, and in Example 4, the carrier was magnesium silicate.

EXAMPLES 5 TO 8

The catalysts were prepared as in Example 1, with the exception that in Example 5, the base was 2,3′ bipyridine (64 µl), in Example 6, the base was 2,4′ bipyridine (0.073 g), in Example 7, the base was 1,10 phenanthroniline (0.093 g), and in Example 8, the base was 2,2-:6,2″ terpyridine (0.109 g).

EXAMPLE 9

The catalyst was prepared in a glass retort by activating a $Ru_3(CO)_{12}$ (0.2 g) and 2,2′ bipyridine (0.15 g) mixture in nitrogen atmosphere at 100° C. On the glass surface was produced an active dark blue complex.

EXAMPLE 10

A catalyst (0.5 g), 1-hexane (1 ml) and toluene (5 ml) as in Example 1 was transferred in a nitrogen atmosphere into an autoclave to which was added 2.5 MPa $H_2$ and 2.5 MPa CO. The autoclave was held for 17 hrs at 423° K. The product was cooled and analyzed with IR and NMR spectrometers and with capillary gas chromatography. The reaction product contained 96% $C_7$ alcohols in which the ratio of the direct chained and the branch chained was 1.1.

EXAMPLE 11

As in Example 10, but for the alkene was used trans-2-hexene. The reaction product contained 97% $C_7$ alcohols (direct chained/branch chained=0.9).

EXAMPLE 12

As in Example 10, but for the alkene was used 1-decene. The reaction product contained 95% $C_{11}$ alcohols.

EXAMPLE 13

As in Example 10, but the temperature was 373° K., The reaction product contained 2% alcohols. The example shows that when a too low hydroformulation temperature is used, the conversion degree remains too low.

EXAMPLE 14

As in Example 10, but with a catalyst (0.5 g) such as in Example 2 and at 373° K. temperature. The reaction product contained 50% $C_7$ alcohols (direct chained/branch chained=2.4).

EXAMPLE 15

As in Example 10, but with the catalyst (0.5 g) as in Example 2 and at 373° K. temperature. The reaction product contained 10% $C_7$ alcohols.

EXAMPLE 16

As in Example 10, but with the catalyst (0.5 g) as in Example 2, at 373° K. temperature, and for the alkene a trans-2-hexene. The reaction product contained 4% $C_7$ alcohols.

EXAMPLE 17

As in Example 10, but with the catalyst (0.5 g) as in Example 3, and at 373° K. temperature. The reaction product contained 2% $C_7$ alcohols.

EXAMPLE 18

As in Example 10, but with the catalyst (0.5 g) as in Example 3, and at 373° K. temperature. The reaction product contained 26% $C_7$ alcohols (direct chained/branch chained=3.5).

EXAMPLE 19

As in Example 10, but with the base as that in Example 10, and at 373° K. temperature. The reaction product contained 60% $C_7$ aldehydes.

EXAMPLE 20

As in Example 10, but with the base as that in Example 6, and at 373° K. temperature. The reaction product contained 18% $C_7$ aldehydes.

EXAMPLE 21

According to Example 10, but with the base as in Example 7, and at 373° K. temperature. The reaction product contained 25% $C_7$ aldehydes and 9% $C_7$ alcohols.

EXAMPLE 22

As in Example 10, but with the base as in Example 8, and at 373° K. temperature. The reaction product contained 25% $C_7$ aldehydes and 11% $C_7$ alcohols.

EXAMPLE 23

As in Example 10, but with the catalyst (0.1 g) as in Example 9, and at 373° K. temperature. The reaction product contained 40% $C_7$ aldehydes and 25% $C_7$ alcohols.

We claim:

1. A process for preparing alcohols and aldehydes from alkenes and synthesis gas selectively by hydroformylation, said process comprising reacting a gas mixture containing alkene, hydrogen and carbon monoxide at a temperature over 360° K. and at a pressure of at least 1 MPa in the presence of a heterogeneous catalyst system composed of a fixed catalyst compound containing a cluster compound $Ru_3(CO)_{12}$ and a heterocyclic nitrogen base selected from the group consisting of 2,2' bipyridine, 2,3' bipyridine, 2,4' bipyridine, 2,2':6,2" terpyridine and 1,10 phenanthroline as a suspension or bound on the surface of a solid carrier.

2. A process according to claim 1, wherein the cluster compound is prepared by activating the mixture of the cluster compound $Ru_3(CO)_{12}$, heterocyclic nitrogen base and fixed carrier by heating at 50° to 200° C.

3. A process according to claim 1, wherein the carrier is a silicon containing compound.

4. A process according to claim 1, wherein the heterocyclic nitrogen base is a 2,2' bipyridine and the fixed carrier is a silica gel.

5. A process according to claim 1, wherein the hydroformylation is performed in a solvent in which the catalyst system is mainly non-soluble.

* * * * *